(12) United States Patent
Watada (10) Patent No.: US 9,339,991 B2
(45) Date of Patent: May 17, 2016

(54) METAL-CERAMIC JOINED BODY

(71) Applicant: KYOCERA Corporation, Kyoto-shi, Kyoto (JP)

(72) Inventor: Kazuo Watada, Koka (JP)

(73) Assignee: KYOCERA Corporation, Kyoto-shi, Kyoto (JP)

( * ) Notice: Subject to any disclaimer, the term of this patent is extended or adjusted under 35 U.S.C. 154(b) by 0 days.

(21) Appl. No.: 14/348,501

(22) PCT Filed: Sep. 28, 2012

(86) PCT No.: PCT/JP2012/075062
§ 371 (c)(1),
(2) Date: Mar. 28, 2014

(87) PCT Pub. No.: WO2013/047740
PCT Pub. Date: Apr. 4, 2013

(65) Prior Publication Data
US 2014/0272457 A1    Sep. 18, 2014

(30) Foreign Application Priority Data

Sep. 30, 2011    (JP) .................................. 2011-216761

(51) Int. Cl.
*B21D 39/00* (2006.01)
*B32B 15/04* (2006.01)
*B23K 1/19* (2006.01)
*C22F 1/18* (2006.01)
*H01R 13/52* (2006.01)
*C22C 14/00* (2006.01)
*C04B 37/02* (2006.01)
*A61N 1/375* (2006.01)
*B23K 35/32* (2006.01)
*H01R 13/405* (2006.01)

(52) U.S. Cl.
CPC .............. *B32B 15/04* (2013.01); *A61N 1/3754* (2013.01); *B23K 1/19* (2013.01); *B23K 35/325* (2013.01); *C04B 37/026* (2013.01); *C22C 14/00* (2013.01); *C22F 1/18* (2013.01); *H01R 13/5224* (2013.01); *B32B 2315/02* (2013.01); *B32B 2535/00* (2013.01); *C04B 2237/125* (2013.01); *C04B 2237/343* (2013.01); *C04B 2237/403* (2013.01); *C04B 2237/84* (2013.01); *H01R 13/405* (2013.01); *Y10T 428/12618* (2015.01)

(58) Field of Classification Search
None
See application file for complete search history.

(56) References Cited

U.S. PATENT DOCUMENTS 3,793,705 A * 2/1974 Cole et al. .................. 228/124.1
6,768,629 B1   7/2004 Allen et al.
7,074,350 B2 * 7/2006 Uchida et al. ................. 252/514

FOREIGN PATENT DOCUMENTS

EP    1484085 A2    5/2004
JP    58-3500 A    1/1983

(Continued)

OTHER PUBLICATIONS

International Search Report, PCT/JP2012/075062, Nov. 6, 2012, 2 pgs.

*Primary Examiner* — Daniel J Schleis
(74) *Attorney, Agent, or Firm* — Volpe and Koenig, P.C.

(57) ABSTRACT

A metal-ceramic joined body is provided in which the surface roughness of the metal is low, and the joined body is unlikely to break. Provided is a metal-ceramic joined body including a metal mainly composed of titanium and a ceramic, in which, regarding the X-ray diffraction peak intensity of a surface portion of the metal excluding a joining region to the ceramic, at least one of $I_{110}$ and $I_{012}$ is larger than $I_{011}$, where $I_{011}$ is the intensity of a peak attributable to a first plane of hexagonal α titanium, $I_{110}$ is the intensity of a peak attributable to a second plane of hexagonal α titanium, and $I_{012}$ is the intensity of a peak attributable to a third plane of hexagonal α titanium.

6 Claims, 3 Drawing Sheets

(56) References Cited

FOREIGN PATENT DOCUMENTS

| JP | 1-149947 A | 6/1989 |
| JP | 9-268368 A | 10/1997 |
| JP | 11-157952 A | 6/1999 |
| JP | 2002-180243 A | 6/2002 |
| JP | 2005-40585 A | 2/2005 |
| JP | 2010-076996 A | 4/2010 |
| JP | 2011-110298 A | 6/2011 |

* cited by examiner

METAL-CERAMIC JOINED BODY

FIELD OF INVENTION

The present invention relates to a metal-ceramic joined body.

BACKGROUND

Currently, medical devices to be placed in the human body, such as implantable pacemakers which correct abnormal movements of the human heart and implantable heart defibrillators, are in practical use. For example, in an implantable pacemaker, a feedthrough terminal is provided on a casing containing a battery, a circuit board, and the like, and an electrode of the feedthrough terminal is connected to a lead which is surgically connected to an appropriate region of the heart. The battery and the circuit board in the casing should not be brought into contact with the tissues of the human body, and the feedthrough is required to reliably prevent bodily fluids from entering the casing in order to prevent operation failures of the pacemaker due to adhesion of bodily fluids to the circuit board and the battery. At the same time, the feedthrough is required to be composed of a highly biocompatible, safe material that does not affect the functions of the human body even if it comes into contact with bodily fluids.

An example of such a feedthrough that is applicable to the living body is described, for example, in Patent Literature 1. In the feedthrough of Patent Literature 1, a housing mainly composed of titanium (Ti) which is a highly biocompatible metal is joined to and surrounds a ceramic member composed of alumina. Through-holes are provided on the ceramic member to which the housing is joined, and conductive pins mainly composed of platinum are inserted through and fixed to the through-holes. Titanium has been used as a highly biocompatible metal and has been increasingly used in a state in which it is joined to a ceramic member, as in the feedthrough described in Patent Literature 1.

CITATION LIST

Patent Literature

PTL 1: Japanese Unexamined Patent Application Publication No. 2010-76966

SUMMARY

Technical Problem

In an existing technique, when a ceramic, such as alumina, and titanium are joined, a metal solder is placed on the joint between the titanium and the ceramic, the titanium and the ceramic are placed in a firing furnace, the temperature is raised to about 1,000° C. over several hours, then cooling is performed, and thereby the titanium and the ceramic are joined by the metal solder.

The transformation temperature of metallic titanium is 882° C. With 882° C. being a boundary temperature, titanium transforms, at lower than 882° C., into an α phase which is hexagonal (hexagonal α titanium), and at 882° C. or higher, into a β phase which is cubic (cubic (β titanium). During brazing, when the temperature is gradually raised so as to exceed 882° C. to about 1,000° C., transformation occurs such that crystals of cubic β titanium grow large. In the subsequent cooling period, all of the crystals gradually transform back to hexagonal α titanium, and in this process, reorganization of titanium further proceeds, resulting in formation of large crystal grains. The existing joined body of a ceramic and titanium is an aggregate of large crystal grains formed in such a manner. Steps and the like occurring at the crystal grain boundaries appear at the surface of titanium, and the surface roughness is high, which is a problem. Furthermore, there may be cases where bonding between crystal grains is weak, and as a result, the joined body may have low toughness and may be relatively likely to break, which is also a problem. The present invention has been achieved in consideration of such problems.

Solution to Problem

In order to overcome the problems described above, the present invention provides a metal-ceramic joined body including a metal mainly composed of titanium and a ceramic, in which, regarding the X-ray diffraction peak intensity of a surface portion of the metal excluding a joining region to the ceramic, at least one of I110 and I012 is larger than I011, where I011 is the intensity of a peak attributable to the (011) plane of hexagonal α titanium, I110 is the intensity of a peak attributable to the (110) plane of hexagonal α titanium, and I012 is the intensity of a peak attributable to the (012) plane of hexagonal α titanium.

Advantageous Effects of Invention

In a metal-ceramic joined body according to the present invention, the surface roughness of the metal mainly composed of titanium is low, and the joined body is relatively unlikely to break.

DETAILED DESCRIPTION OF THE PREFERRED EMBODIMENTS

Figure 1:
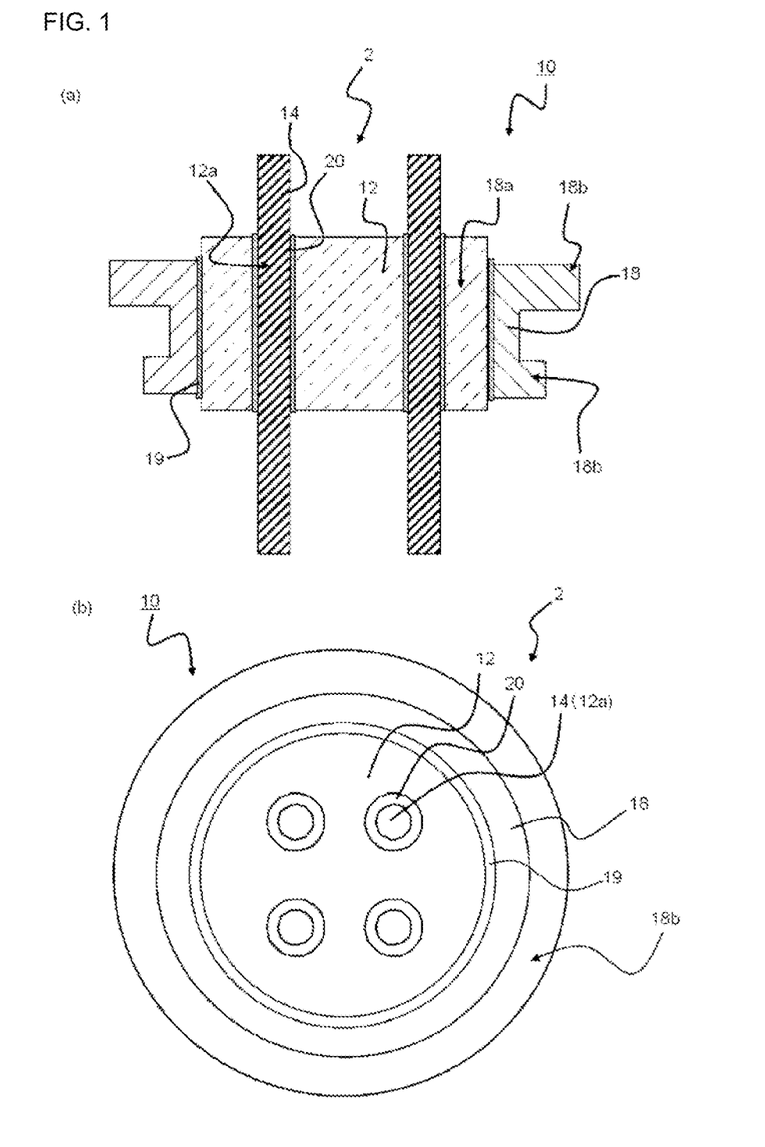
FIG. 1(a) is a schematic sectional view showing a feedthrough 10 which includes a metal-ceramic joined body according to an embodiment of the present invention.
FIG. 1(b) is a schematic top view of the feedthrough 10.
Figure 2:
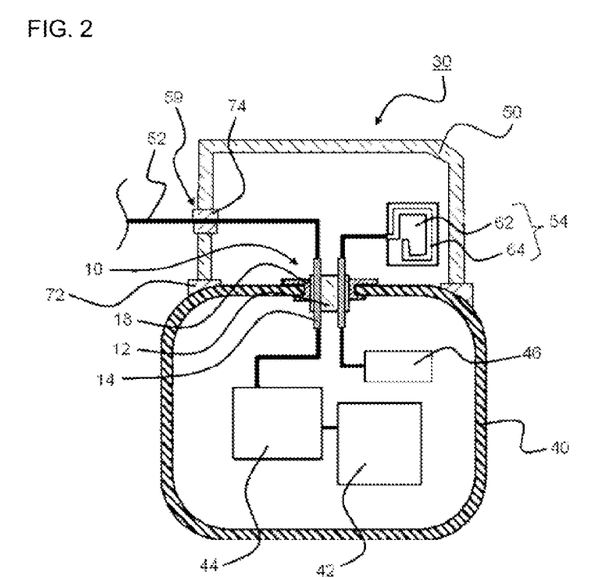
FIG. 2 is a schematic sectional view of a pacemaker 30 including the feedthrough 10 shown in FIG. 1.

Embodiments of the present invention will be described in detail below. FIG. 1(a) is a schematic sectional view showing a feedthrough 10 which includes a metal-ceramic joined body according to an embodiment of the present invention, and FIG. 1(b) is a schematic top view of the feedthrough 10. FIG. 2 is a schematic sectional view of a pacemaker 30 including the feedthrough 10 shown in FIG. 1.

The feedthrough 10 according to this embodiment includes a round columnar ceramic 12 (also referred to as "ceramic body 12") mainly composed of, for example, alumina (Al2O3), conductive pins 14, and a biocompatible metal 18

(also referred to as "housing 18") mainly composed of titanium. The ceramic body 12 has a diameter of about 3 mm and a height of about 2 mm.

The feedthrough 10 is used by being fixed to, for example, a pacemaker 30 shown in FIG. 2. Note that the contents of elements shown below can be obtained by a method in which, using PHOENIX manufactured by EDAX Inc., spectra corresponding to the individual atoms are obtained at an accelerating voltage of 15 kV, and the contents are calculated from spectral intensities corresponding to the individual atoms.

The ceramic body 12 is provided with a plurality of through-holes 12a passing therethrough from the upper surface (upper principal surface in FIG. 1(a)) toward the lower surface (lower principal surface in FIG. 1(a)). The alumina content in the ceramic body 12 is 50% by mass or more, and is preferably, for example, 90% by mass or more.

The conductive pins 14 are composed of an alloy containing 90% by mass of platinum and 10% by mass of iridium (Ir). The conductive pins 14 may contain, in addition to platinum and iridium, a substance having good biocompatibility, such as palladium (Pd), ruthenium (Ru), or rhodium (Rh). Furthermore, the conductive pins may contain, as a main component, palladium, ruthenium, rhodium, iridium, or the like. A conductive pin 14 is inserted through a through-hole 12a of the ceramic body 12, and the inner surface of the through-hole 12a and the conductive pin 14 are joined by a joining portion 20. The joining portion 20 is a brazing material layer mainly composed of a noble metal, such as a gold solder containing, as a main component, gold (Au). Hereinafter, a structure including the ceramic body 12 and the conductive pins 14 which are integrated by joining with the joining portions 20 may be referred to as a pin member 2. The conductive pin 14 has a diameter of about 0.3 mm, and the through-hole 12a of the ceramic body 12 has a diameter of about 0.4 mm.

The housing 18 is a cylindrical member having a through-hole 18a, and includes flange portions 18b provided at both ends along the through-hole. The pin member 2 is placed in the through-hole 18a of the housing 18, and the outer peripheral surface of the ceramic body 12 of the pin member 2 and the outer peripheral surface 18a of the housing 18 are joined by a joining portion 19. The joining portion 19 is, for example, a gold solder layer mainly composed of gold. The metal brazing material is melted by being heated, for example, to 1,000° C. or higher and then becomes solidified between the ceramic body 12 and the housing 18, and thus the joining portion 19 joins the ceramic body 12 and the housing 18.

Regarding the X-ray diffraction peak intensity of the surface portion of the housing 18 excluding a joining region to the ceramic body 12, at least one of I110 and I012 is larger than I011, where I011 is the intensity of a peak attributable to the (011) plane of hexagonal α titanium, I110 is the intensity of a peak attributable to the (110) plane of hexagonal α titanium, and I012 is the intensity of a peak attributable to the (012) plane of hexagonal α titanium. The joining region to the ceramic body 12 refers to a region of the surface of the housing 18 to which the joining portion 19 adheres.

Note that the X-ray diffraction peak intensity can be measured, for example, using an Empyrean PW6003/00 manufactured by Spectris Co., Ltd. as a diffractometer, under the following conditions. First, the surface portion of the housing 18 is measured by an X-ray diffraction method using a CuKα ray to determine the intensity I011 of a peak attributable to the (011) plane of hexagonal α titanium, the intensity I110 of a peak attributable to the (110) plane of hexagonal α titanium, the intensity I012 of a peak attributable to the (012) plane of hexagonal α titanium, and the intensity I013 of a peak attributable to the (013) plane of hexagonal α titanium. Regarding the X-ray diffraction pattern of hexagonal α titanium, it is possible to refer to the code 00-044-1294 in the PDF (Powder Diffraction Datafile, Publication title: On the determination of high-purity alpha-titanium lattice parameters) published by the International Centre for Diffraction Data (ICDD).

According to the PDF code 00-044-1294, for the X-ray diffraction peak attributable to the (011) plane of hexagonal α titanium, the lattice spacing is 2.24289 Å, and the diffraction angle 2θ is 40.173°; for the X-ray diffraction peak attributable to the (110) plane, the lattice spacing is 1.47550 Å, and the diffraction angle 2θ is 62.941°; for the X-ray diffraction peak attributable to the (012) plane, the lattice spacing is 1.72564 Å, and the diffraction angle 2θ is 53.024°; and for the X-ray diffraction peak attributable to the (013) plane, the lattice spacing is 1.33133 Å, and the diffraction angle 2θ is 70.704°.

In some cases, the lattice spacings and diffraction angles 2θ described in the PDF code 00-004-1294 for hexagonal α titanium may vary depending on the difference in the measuring apparatus, the measurement error, and the like. The lattice spacing of the peak attributable to the (011) plane may vary between 2.22 and 2.26 Å, the lattice spacing of the peak attributable to the (110) plane may vary between 1.46 and 1.50 Å, the lattice spacing of the peak attributable to the (012) plane may vary between 1.71 and 1.75 Å, and the lattice spacing of the peak attributable to the (013) plane may vary between 1.31 and 1.36 Å. Using an X-ray diffractometer, the X-ray diffraction intensity is measured, for example, at a diffraction angle 2θ in a range of 10° to 90°, and the peak intensity in the range including the lattice spacing corresponding to each plane is defined as the intensity of the peak attributable to the plane. Using the intensities I011, I110, I012, and I013 of the peaks attributable to the planes thus measured, the ratio of each of intensities I110, I012, and I013 to the intensity I011 of the peak attributable to the plane can be calculated.

For example, normal titanium, which is not highly oriented in a specific plane direction, is in a normal hexagonal α titanium state at lower than 882° C. Regarding the X-ray diffraction peak intensity of normal hexagonal α titanium which is not highly oriented in a specific plane direction, it is known that, assuming I011 is 100, I110 is about 15 and I012 is about 13. Thus, each of I110 and I012 is a small value of less than ⅕ of I011.

The housing 18 mainly composed of titanium in this embodiment is characterized in that at least one of I110 and I012 is larger than I011. That is, in the housing 18, titanium is believed to be highly oriented in the (110) plane and the (012) plane. The (110) plane and the (012) plane of titanium are non-slip planes in metal crystals, and in the housing 18 which is highly oriented in the non-slip planes, plastic deformation is unlikely to occur compared with the normal hexagonal α titanium. The housing 18 is unlikely to be deformed under external force.

In addition, regarding the X-ray diffraction peak intensity of the housing 18 in this embodiment, I013 is larger than I011, where I013 is the intensity of a peak attributable to the (013) plane of hexagonal α titanium. The (013) plane is also a non-slip plane, and the housing 18 is unlikely to be deformed.

Furthermore, regarding the full width at half maximum of the X-ray diffraction peak of the housing 18, at least one of the full width at half maximum of the peak attributable to the (110) plane of hexagonal α titanium and the full width at half maximum of the peak attributable to the (012) plane of hexagonal α titanium is smaller than 0.2°. Thus, the housing 18 has relatively small full widths at half maximum of the X-ray diffraction peaks attributable to planes, and the peaks are steep. The crystals contained in the housing 18 are in a highly crystalline state in which regularity in the arrangement of atoms is high. That is, the housing 18 has high crystallinity and is unlikely to be deformed.

When the housing 18 mainly composed of titanium is joined to the ceramic body 12, it is subjected to heat treatment. That is, in the process of forming a joining portion 19 which joins the housing 18 and the ceramic body 12, the housing 18 is subjected to heat treatment, for example, at about 1,100° C. In the ordinary heat treatment performed in the field of metal-ceramic joining technology, the temperature is raised to about 1,100° C., which exceeds the transformation temperature of titanium of 882° C., over a long period of time from several tens of minutes to several hours. When the metal mainly composed of titanium is subjected to the ordinary heat treatment, titanium is entirely transformed into cubic β titanium, and then is transformed back to a hexagonal α titanium phase. In this process, reorganization of titanium gradually proceeds, and crystals become large more than necessary. Furthermore, crystals formed by the conventional heat treatment, in which the temperature is raised to about 1,000° C. over a long period of time from several tens of minutes to several hours, are not cubic β titanium or hexagonal α titanium, but are close to titanium in an amorphous stat. The crystals are not likely to be oriented in a specific plane orientation.

In this embodiment, the housing 18 and the ceramic body 12 are joined by the joining portion 19, for example, composed of a Au solder. In the heat treatment for forming the joining portion 19, the time required for raising the temperature to 1,100° C. is set to be extremely short, such as about 1 to 1.5 minutes. Furthermore, after the temperature is raised in such an extremely short period of time, the temperature is lowered to 882° C. or lower in a short period of time, such as less than 1 minute. In this embodiment, in the heat treatment for forming the joining portion 19 which joins the housing 18 and the ceramic body 12, the period of time in which the temperature exceeds 882° C., i.e., the transformation temperature of titanium, is set to be less than 2 minutes in total. By raising the temperature in such a short period of time, titanium originally in a hexagonal α titanium state is prevented from growing large as crystals in a cubic β titanium state. Furthermore, since the temperature is lowered in a short period of time, during the transformation from cubic β titanium to hexagonal α titanium, movement of atoms constituting titanium is rapidly suppressed, and the crystal state is changed to a neighborhood stable state without long-distance movement. The stable state thus brought about is assumed to be the state of hexagonal α titanium which is highly oriented in the (110) plane and the (012) plane.

Such rapid heating can be achieved by a rapid heating apparatus or the like that has not been used in the field of metal-ceramic joining. Examples of the rapid heating apparatus include an infrared rapid heating apparatus in which an infrared heating unit and a reflecting mirror are combined, the reflecting mirror condensing thermal energy (infrared radiation) emitted from the infrared heating unit locally onto a certain narrow region. By placing an assembly including the housing 18 composed of titanium, the ceramic body 12, and a metal solder, which is a precursor for the joining portion 19, for example, on a condensing portion in the infrared rapid heating apparatus, the temperature of the entire assembly can be rapidly raised. Furthermore, in such an infrared rapid heating apparatus, only the assembly is locally heated by infrared radiation condensed by the reflecting mirror. Therefore, in particular, the temperature of the atmosphere other than the condensing portion can be maintained relatively low compared with the temperature of the assembly placed on the condensing portion, and the temperature of the entirety can be rapidly lowered as heating (irradiation with infrared radiation) is stopped.

In general, in the field of metal-ceramic joining, it is regarded as important to efficiently perform heat treatment on a large number of parts at a time. Accordingly, it has been a common practice to use, as a heating apparatus for joining a metal and a ceramic, a heating furnace having the largest possible capacity, in which the temperature is gradually raised or lowered while uniformly controlling the temperature. The infrared rapid heating apparatus described above rapidly heats a limited narrow region in a short period of time, and is completely different from the heating furnace or the like that has been generally used in the field of metal-ceramic joining. The metal-ceramic joined body according to the present application has been found for the first time by the present inventor through trial and error experiments.

In the feedthrough 10, each of the conductive pins 14 mainly composed of Pt, the housing 18 composed of titanium, and the joining portions 20 and 19 mainly composed of a noble metal is composed of a highly biocompatible component. In the case where the feedthrough 10 is used for a device to be placed in the human body, such as a pacemaker, even if the feedthrough 10 is brought into contact with bodily fluids, the human body is less likely to be affected.

The metal having relatively high biocompatibility refers to a metal in which body's immune reactions, in particular, thrombus formation and electrode encapsulation caused by fibrosed cellular tissue are less likely to occur even if brought into contact with the cellular tissue of the body and blood. Examples thereof include gold (Au), platinum (Pt), titanium (Ti), niobium (Nb), boron (B), and the like. Furthermore, noble metals, such as palladium (Pd), ruthenium (Ru), rhodium (Rh), and iridium (Ir), which have a relatively high melting point and are chemically stable, have also relatively high biocompatibility.

FIG. 2 is a schematic sectional view of a pacemaker 30 including the feedthrough 10 shown in FIG. 1. The pacemaker 30 has a structure in which a lower case 40 and an upper case 50 are combined. The lower case 40 contains a battery 42, a circuit board 44, an EMI filter 46, and the like, and the feedthrough 10 is fixed on the upper wall of the lower case 46. A lead 52 connected to a conductive pin 14 of the feedthrough 10 passes inside the upper case 50 and an antenna 54 connected to another conductive pin 14 of the feedthrough 10 is disposed inside the upper case 50.

The lower case 40 is a housing, for example, composed of titanium, and has an opening on the wall thereof on the upper side in FIG. 2. The feedthrough 10 is disposed so as to occlude the opening, and the housing 18 of the feedthrough 10 and the lower case 40 are welded together. The lower case 40 contains the battery 42, for example, a lithium-ion battery, the circuit board 44 which is connected to the battery 42 and generates a predetermined electrical signal, and the EMI filter 46 for removing EMI (electro-magnetic interference), for example, due to electromagnetic waves from television transmitters, mobile phones, towers, and the like. The battery 42, the circuit board 44, and the EMI filter 46 are separated from bodily fluids, such as blood, by the lower case 40 and the feedthrough 10.

The upper case 50 is, for example, composed of a highly biocompatible resin material. The upper case 50 has a shape of a container provided with an opening on the lower side in the drawing, and the opening on the lower side in the drawing is occluded by the lower case 40. A sealing member 72 composed of a highly biocompatible material, which prevents bodily fluids from entering the upper case 50, is disposed at the contact portion between the upper case 50 and the lower case 40. The antenna 54 is disposed in the internal space surrounded by the inner surface of the upper case 50 and the upper surface of the lower case 40 on the upper side in the drawing. Furthermore, a plurality of openings 59 are provided on part of the wall of the upper case 50, and leads 52 are inserted through the openings. A sealing member 74 composed of a highly biocompatible material, which prevents bodily fluids from entering the upper case 50, is disposed at the openings 52 of the upper case 50.

In the feedthrough 10, the conductive pins 14 are inserted through the through-holes 12a of the ceramic body 12. The circuit board 44 in the lower case 40 and the lead 52 passing through the upper case 50 are physically and electrically connected to each other through the conductive pin 14. The lead 52 is electrically connected to a predetermined position in the heart of the human body, and guides an electrical signal, which is generated from the circuit board 44 and supplied through the conductive pin 14, to the predetermine position in the heart of the human body. The antenna 54 is also disposed in the upper case 50, and the antenna 54 is connected to the circuit board 44 in the lower case 40 through the conductive pin 14 of the feedthrough 10.

The antenna 54 sends and receives various data, such as data showing the operational status of the pacemaker 30, data for adjusting the operating conditions of the pacemaker 30, and data showing the health status of the human body with the pacemaker 30 inside, to and from an external communication device. The antenna 54 is also connected to the circuit board 44 in the lower case 40 through the conductive pin 14 of the feedthrough 10, sends signals from the circuit board 44, and sends signals received from the external communication device to the circuit board 44. The antenna 54, for example, has a structure in which a conductive pattern 64 is disposed on the surface of a ceramic substrate 62. In the case where the antenna 54 has such a structure, the production process is simplified compared with a case where an antenna is formed by a metal wire, the pacemaker can be fabricated with low costs, and the conductive pins of the feedthrough can be prevented from being applied with external force as a result of bending of the metal wire.

As described above, the feedthrough 10 is composed of a highly biocompatible metal material, and safety to the human body is relatively high even when the feedthrough 10 is disposed in the human body. Furthermore, in the feedthrough 10 including the metal-ceramic joined body according to this embodiment, the housing 18 composed of titanium is unlikely to be deformed. For example, even in the case where a person having the heart pacer 30 repeats vigorous movement continuously over a long period of time, it is possible to satisfactorily maintain the joining state between the housing 18 and the ceramic body 12. Furthermore, since the housing 18 is unlikely to be deformed, the joining state between the housing 18 and the lower case 40 is satisfactorily maintained, and a gap or the like is prevented from occurring between the housing 18 and the lower case 40.

The feedthrough 10 can be produced, for example, by the method described below.

First, a ceramic body 12 mainly composed of alumina is prepared, the ceramic body 12 being provided with a plurality of through-holes 12a passing therethrough from the upper surface toward the lower surface. The ceramic body 12 can be produced, for example, by a known method in which alumina powder is press-formed, followed by firing. Although the material for the ceramic body is not limited to alumina, in view of biocompatibility, alumina, barium titanate, zirconia, silicon nitride, or the like is preferable.

A metallization layer is formed on the inner surfaces of the through-holes 12a and the outer peripheral surface of the ceramic. The metallization layer on the inner surfaces of the through-hole 12a may be formed by a known method, such as sputtering or a paste method.

Figure 3:
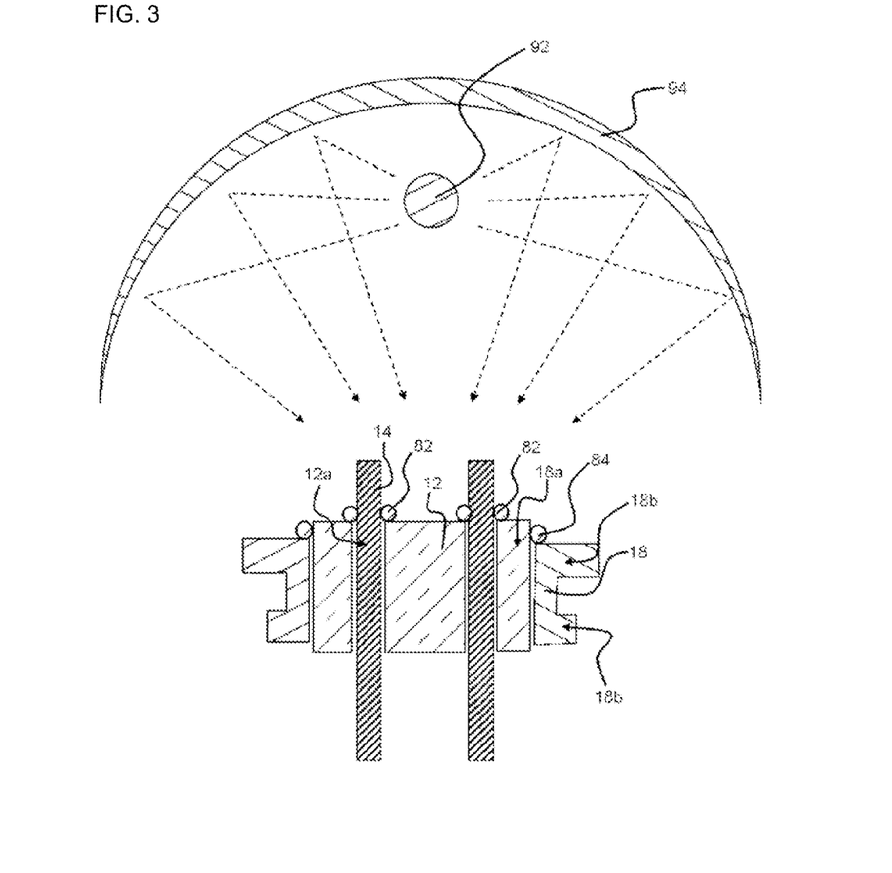
FIG. 3 is a schematic diagram illustrating a part of process of manufacturing the feedthrough 10 shown in FIGS. 1 and 2, and showing a state in which the individual members are disposed in a rapid heating furnace.

Next, using a jig (not shown), the individual members are placed in an infrared rapid heating apparatus such that they are disposed at predetermined positions, and are entirely subjected to heat treatment. FIG. 3 is a schematic diagram showing a state in which the individual members are disposed in a heating furnace of an infrared rapid heating apparatus. The infrared rapid heating apparatus includes an infrared radiator 92, such as a known infrared lamp, and a reflecting mirror 94 configured to condense thermal energy (infrared radiation) emitted from the infrared heating unit locally onto a certain narrow region.

As shown in FIG. 3, the individual members are held by a jig (not shown) such that the conductive pins 14 are inserted through the through-holes 12a whose inner surfaces are coated with a metallization layer (not shown), and the ceramic body 12 is placed in the through-hole 18a of the housing 18. Furthermore, a ring-shaped first gold solder material 82 mainly composed of Au is placed so as to cover the upper openings between the through-holes 12a and the conductive pins 14, and a ring-shaped second gold solder material 84 mainly composed of Au is placed so as to cover the upper portion of the gap between the ceramic body 12 and the housing 18. In such a state, all of the members are placed on a heating portion of the infrared rapid heating apparatus, i.e., a portion to which infrared radiation is condensed by the reflecting mirror 94. Note that FIG. 3 schematically shows the structure of the infrared rapid heating apparatus. In FIG. 3, the infrared radiator 92 and the reflecting mirror 94 are shown rather small relative to the ceramic body 12 and the housing 18.

In this state, for example, the entirety is heated to 1,100° C. over 1 to 5 minutes, then the temperature is maintained at 1,100° C. for 10 seconds, and natural cooling is performed for about 10 seconds to 1 minute until 882° C., and for about 15 minutes until 200° C. The melting point of Au constituting the first gold solder material 82 and the second gold solder material 84 is about 1,060° C. During the heat treatment, the first gold solder material 82 and the second gold solder material 84 are melted and spread over the entire gaps between the conductive pins 14 and the though-holes 12a and the entire gap between the ceramic body 12 and the housing 18, and as the temperature is lowered, the gold solder materials 82 and 84 solidify. Thereby, joining portions 20 and a joining portion 19 are formed. The feedthrough 10 can be fabricated in such a manner.

EXAMPLES

Figure 4:
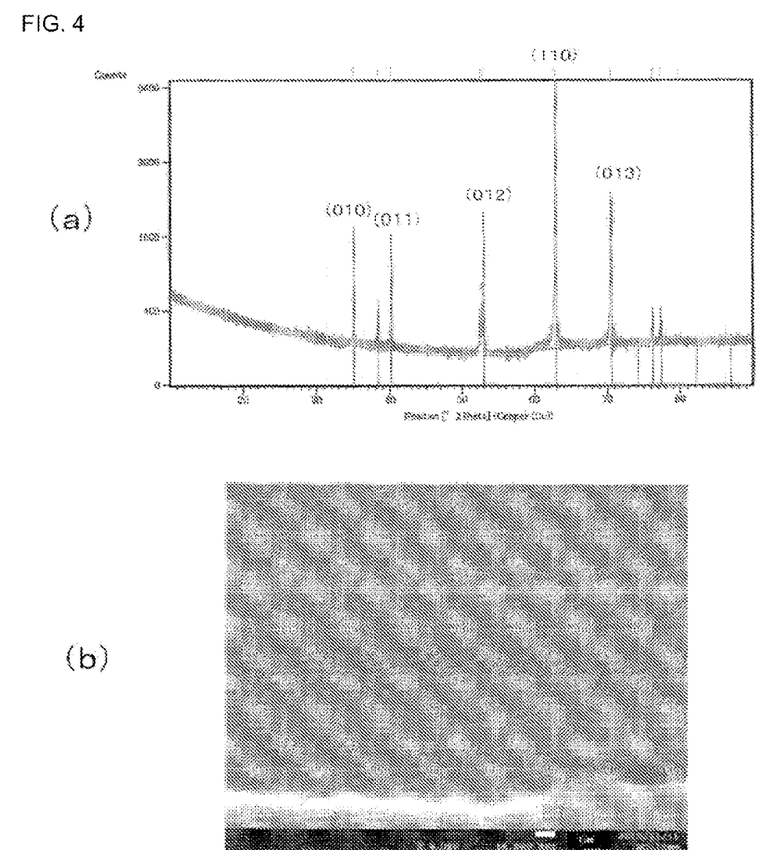
FIG. 4(a) shows an intensity data of X-ray diffraction of the metal according to an embodiment of the present invention.
FIG. 4(b) is an electron micrograph of the sample shown in FIG. 4(a).

Examples of the present invention will be shown below, and an example of advantageous effects of the present invention will be described. FIG. 4(a) shows X-ray diffraction intensity spectrum data for the housing 18 of the feedthrough 10 fabricated by the process described above. The data of FIG. 4(a) was obtained by measurement with the X-ray output at 45 kV and 40 mA, using "Empyrean PW6003/00" manufactured by Spectris Co., Ltd. as an X-ray diffractometer. As shown in FIG. 4(a), in the housing 18 of this example, I110 and I012 are larger than I011, thus confirming that titanium is highly oriented in the (110) plane and the (012) plane. Furthermore, I013 is larger than I011. The full width at half maximum of I110 is 0.101 Å, and the full width at half maximum of I012 is 0.102 Å. As is evident from FIG. 4(a), the peaks are steep, thus confirming high crystallinity.

FIG. 4(b) is a photograph of a secondary electron image of the surface of the sample shown in FIG. 4(a). As a device, "JSM-7001F" manufactured by JEOL Ltd. was used, and electrons were accelerated at 15 kV. It can be confirmed that no substantial deformation is observed in the housing, and the surface of the housing is relatively smooth.

Figure 5:
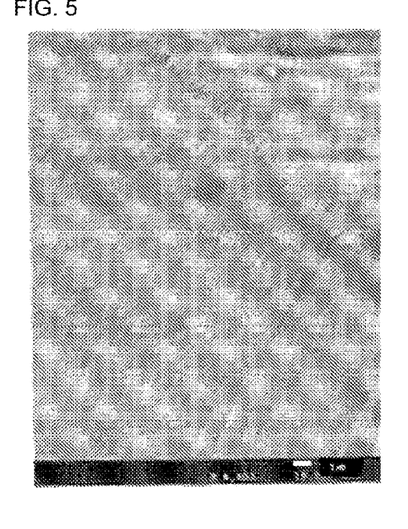
FIG. 5 is an electron micrograph of an existing metal-ceramic joined body.

Furthermore, FIG. 5 is a photograph of a comparative example and shows a surface of a metal mainly composed of titanium in an existing metal-ceramic joined body. The device used for photographing and photographing conditions are the same as those for the photograph shown in FIG. 4(b). The existing metal-ceramic joined body was produced by joining using MINI-VAC-II manufactured by Tokyo Vacuum Co., Ltd., which is one of common vacuum furnaces used in the field of metal-ceramic joining technology. The temperature profile was set such that the temperature was raised to 1,100° C. over 130 minutes, then the temperature was maintained at 1,100° C. for one minute, and natural cooling was performed to 880° C. or lower over about 11 minutes and to 200° C. over about 5 hours. In the case where the conventional furnace is used, it can be confirmed that large irregularities appear on the surface of the housing. Furthermore, the X-ray diffraction intensity spectrum was measured under the same conditions as those in the example described above. The results showed the same tendency as that in the X-ray diffraction peak intensity of ordinary hexagonal α titanium, in which I110 and I012 were each smaller than I011. Furthermore, since the peak intensities were low and the peaks were not steep, calculations of full widths at half maximum of I110 and I012 were unclear. That is, in the sample produced using the conventional furnace, the crystallinity was very low.

Furthermore, Table 1 below shows the evaluation results on the mechanical strength of a metal mainly composed of titanium in a metal-ceramic joined body. In each sample shown in Table 1, only the metal mainly composed of titanium is subjected to heat treatment, and the metal and the ceramic are not joined. Specifically, the elongation at break and the tensile strength according to JIS Z2201 (corresponding to ISO 6892 "Metallic-Tensile testing") were measured using a universal tensile testing instrument RTC-1350A manufactured by A & D Co., Ltd., in which a 25 kN load cell was used, the loading rate was set at 5 mm/min, the gauge length was set at 50 mm, and the distance between chucks was set at 97 mm. Samples with a shape in compliance with No. 13B of JIS Z2201 were used for the measurements.

TABLE 1

|  |  | Tensile strength | | Elongation at break |
|---|---|---|---|---|
|  |  | (kN) | (N/mm2) | (%) |
| Conventional vacuum furnace | Sample 1 | 13.49 | 360.49 | 20.0 |
|  | Sample 2 | 13.82 | 371.29 | 36.6 |
|  | Sample 3 | 13.73 | 366.97 | 32.2 |
|  | Average | 13.68 | 366.25 | 29.6 |
| Infrared rapid heating apparatus | Sample 1 | 14.64 | 395.78 | 47.6 |
|  | Sample 2 | 14.54 | 393.29 | 49.2 |
|  | Sample 3 | 14.57 | 393.76 | 50.2 |
|  | Average | 14.58 | 394.28 | 49.0 |

The samples 1 to 3 under the row titled "Infrared rapid heating apparatus" in Table 1 show the measurement results of the tensile strength and elongation at break on titanium members heat-treated using the same infrared rapid heating apparatus as that used for heat treatment of the sample shown in the photograph of FIG. 4(b) under the same conditions as those for the sample shown in FIG. 4(b). Furthermore, the samples 1 to 3 under the row titled "Conventional vacuum furnace" in Table 1 show the measurement results of the tensile strength and elongation at break on titanium members heat-treated using the same conventional vacuum heat treatment apparatus as that used for heat treatment of the sample shown in the photograph of FIG. 5 under the same conditions as those for the sample shown in FIG. 5. Each of the samples shown in Table 1 was obtained by subjecting only the metal mainly composed of titanium, excluding the ceramic, in order to measure the mechanical strength. The samples 1 to 3 by the "infrared rapid heating apparatus" were subjected to the same heat treatment as that for the metal of the metal-ceramic joined body shown in FIG. 4(b), and thus, it is believed that the results well represent the mechanical properties of titanium in the metal-ceramic joined body shown in FIG. 4(b). Furthermore, the samples 1 to 3 by the "conventional vacuum furnace" were subjected to the same heat treatment as that for the metal of the metal-ceramic joined body shown in FIG. 5, and thus, it is believed that the results well represent the mechanical properties of titanium in the metal-ceramic joined body shown in FIG. 5.

As shown in Table 1, the samples heat-treated with the "infrared rapid heating apparatus" have a higher tensile strength and a larger elongation at break than the samples heat-treated with the "conventional vacuum furnace". That is, the titanium of the samples heat-treated with the "infrared rapid heating apparatus" is unlikely to be broken even when a relatively large external force is applied, and has high reliability. The feedthrough 10 according to this embodiment shows a slow degradation with time due to residual stress of the housing 18, for example, caused during welding of the housing 18 of the feedthrough 10 and the lower case 40. Even when external forces are applied in various processes, such as the welding, the failure probability due to the stress is low.

The metal-ceramic joined body of the present invention has been described. However, it is to be understood that the present invention is not limited to the embodiments described above, and various improvements and modifications can be made within a range not deviating from the gist of the present invention.

REFERENCE SIGNS LIST 10 feedthrough
12 ceramic body
12a through-hole
14 conductive pin
18 housing
19, 20 joining portion
30 pacemaker
40 lower case
42 battery
44 circuit board
46 EMI filter
52 lead
54 antenna

What is claimed is:

1. A metal-ceramic joined body comprising a metal mainly composed of titanium, and a ceramic,
wherein, regarding the X-ray diffraction peak intensity of a surface portion of the metal excluding a joining region to the ceramic, at least one of $I_{110}$ and $I_{012}$ is larger than $I_{011}$, where $I_{011}$ is the intensity of a peak attributable to the (011) plane of hexagonal α titanium, $I_{110}$ is the intensity of a peak attributable to the (110) plane of hexagonal α titanium, and $I_{012}$ is the intensity of a peak attributable to the (012) plane of hexagonal α titanium.

2. The metal-ceramic joined body according to claim 1, wherein both the $I_{110}$ and the $I_{012}$ are larger than the $I_{011}$.

3. The metal-ceramic joined body according to claim 1, wherein $I_{013}$ is larger than the $I_{011}$, where $I_{013}$ is the intensity of a peak attributable to the (013) plane of hexagonal α titanium.

4. The metal-ceramic joined body according to any one of claim 1, wherein, regarding the full width at half maximum of the X-ray diffraction peak of the metal, at least one of the full width at half maximum of the peak attributable to the (110) plane of hexagonal α titanium and the full width at half maximum of the peak attributable to the (012) plane of hexagonal α titanium is smaller than 0.2°.

5. The metal-ceramic joined body according to any one of claim 1, wherein the metal and the ceramic are joined by a metal solder.

6. The metal-ceramic joined body according to claim 5, wherein the metal solder is mainly composed of gold.

* * * * *